(12) United States Patent
Worrel (10) Patent No.: US 11,607,322 B2
(45) Date of Patent: Mar. 21, 2023

(54) GRAFT COMPRESSION SYSTEM (71) Applicant: Daniel A. Worrel, Dallas, TX (US)

(72) Inventor: Daniel A. Worrel, Dallas, TX (US)

(73) Assignee: SUREMKA, LLC, Dallas, TX (US)

( * ) Notice: Subject to any disclaimer, the term of this patent is extended or adjusted under 35 U.S.C. 154(b) by 413 days.

(21) Appl. No.: 16/779,584

(22) Filed: Feb. 1, 2020

(65) Prior Publication Data

US 2020/0246161 A1 Aug. 6, 2020

Related U.S. Application Data (60) Provisional application No. 62/800,134, filed on Feb. 1, 2019.

(51) Int. Cl.
*A61F 2/46* (2006.01)
*A61F 2/08* (2006.01)
(Continued)

(52) U.S. Cl.
CPC .......... *A61F 2/4601* (2013.01); *A61F 2/0811* (2013.01); *A61F 2/0805* (2013.01);
(Continued)

(58) Field of Classification Search
CPC ........ A61F 2/4601; A61F 2/0811; A61F 2/08; A61F 2/0805; A61F 2/9524; A61F 2/07; A61F 2/95; A61F 2/9525; A61F 2/9526; A61F 2/9522; A61F 2/2433; A61L 27/3622; B25B 27/10; B21D 41/00; B21D 41/04; B21D 41/045
(Continued)

(56) References Cited

U.S. PATENT DOCUMENTS 6,167,605 B1   1/2001  Morales
8,640,521 B2   2/2014  Righini
(Continued)

FOREIGN PATENT DOCUMENTS

WO   01/35861 A1   5/2001
WO   03/079933 A1  10/2003

OTHER PUBLICATIONS

International Search Report and Written Opinion for International Patent No. PCT/US2020/016297 filed Feb. 1, 2020; 8 pgs.

*Primary Examiner* — Marcela I. Shirsat (57) ABSTRACT

A graft compression system for compressing soft tissue grafts used in connection with reconstructive surgery on the anterior cruciate ligament (ACL). The graft compression system includes a compression chamber having an elongate hollow shaft body having two ends that are threaded to mate with correspondingly threaded collet nuts. Collets are removably inserted into, and engage, the collet nuts fastened to opposing ends of the compression chamber A surgical graft may be inserted into a hollow compression tube having a lumen with a compressible diameter, said compression tube being sized for insertion into the collets and compression chamber. When such collet nuts are tightened by a user of the graft compression system, the inner diameters of the respective collet nuts nested within such collet nuts are decreased, causing the diameter of the lumen of the hollow compression tube to in turn be decreased and compress the surgical graft within.

5 Claims, 9 Drawing Sheets (51) Int. Cl.
*A61F 2/24* (2006.01)
*A61F 2/95* (2013.01)
*A61L 27/36* (2006.01)

(52) U.S. Cl.
CPC ........... *A61F 2/2433* (2013.01); *A61F 2/9524* (2020.05); *A61F 2/9526* (2020.05); *A61L 27/3662* (2013.01)

(58) Field of Classification Search
USPC ........ 606/60, 1, 108, 198; 600/36; 623/1.13, 623/1.23, 1.36, 13.11, 13.15; 72/370.25, 72/462, 402
See application file for complete search history.

(56) References Cited

U.S. PATENT DOCUMENTS

| | | |
|---|---|---|
| 2010/0168835 A1 | 7/2010 | Dorn |
| 2013/0030418 A1 | 1/2013 | Taft |
| 2013/0152659 A1* | 6/2013 | Maimon ............... A61F 2/2433 72/402 |

* cited by examiner

GRAFT COMPRESSION SYSTEM

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to systems and devices for use in conjunction with surgical techniques, and more specifically, to a graft compression system for compressing soft tissue grafts used in connection with reconstructive surgery on the anterior cruciate ligament (ACL).

2. Description of Related Art Including Information Disclosed Under 37 CFR 1.97 and 1.98

The anterior cruciate ligament (ACL) is one of four main ligaments of the human knee. The ACL works to resist, among other things, anterior tibial translation and rotational loads on the knee. This function prevents anterior tibial subluxation of the lateral and medial tibiofemoral compartments that accounts for what is known the "pivot-shift phenomena." An ACL tear is one of the most common knee injuries, with over 100,000 ACL tears occurring in the U.S. annually. When an ACL tear occurs, most patients will require ACL reconstruction surgery, which generally involves the removal of the torn or ruptured ACL, and the replacement with a piece of tendon or ligament from the patient or from a donor.

Traditional ACL surgery typically involves the preparation of a soft-tissue tendon graft having a particular diameter, which is positioned within a bone tunnel drilled by the surgeon, the bone tunnel typically sized to have a diameter approximately equal to the diameter of the graft. The graft is then secured to the patient's bones with screws or other fixation devices such as buttons. The graft will then serve as scaffolding on which new ligament tissue can grow. Drawbacks to traditional ACL reconstruction surgical techniques include the increased occurrence of less than optimal healing environments and tissue recovery, as well as increased micro-motion between the graft and bone, which stimulates the formation of a fibrous, mechanically inferior scar. These complications can result in more tissue trauma, increased swelling, more pain for the patient, and slower rehabilitation. Such complications arising from traditional ACL surgery, as outlined above, can be caused by the significant volume of the bone tunnel drilled by the surgeon. Occurrences of graft failure following traditional ACL surgery is also known to sometimes arise from surgeons utilizing traditional methods of graft fixation.

What is needed is a system for compressing soft tissue tendon grafts that can be easily sterilized prior to surgery, and manually operated by surgeons and/or other operating room personnel to prepare grafts having substantially reduced diameters for use in both traditional and less invasive ACL reconstruction surgery (including "All Inside" ACL surgery). Soft tissue grafts having substantially reduced diameters, with volumes reduced by 50% or more, will in turn allow for the substantial reduction in the volume of bone tunnels/sockets that must be drilled during surgery (resulting in less trauma to the patient, pain, and swelling). The compression of soft tissue tendon grafts will also allow, once the graft rehydrates, for the creation of a biologic compressive fit. This biologic compressive fit will minimize micro-motion, assist in tissue recovery, and improve the healing environment. The creation of a biologic compressive fit will also make it unnecessary for surgeons to use interference screws and buttons to affix the graft (leading to fewer complications of the type outlined above). The graft compression system disclosed herein satisfies these needs and others as will become apparent to one of ordinary skill after a careful study of the detailed description and embodiments.

BRIEF DESCRIPTION OF THE SEVERAL VIEWS OF THE DRAWINGS

The present invention will be more fully understood by reference to the following detailed description of the preferred embodiments of the present invention when read in conjunction with the accompanying drawings, wherein.

The above figures are provided for the purpose of illustration and description only, and are not intended to define the limits of the disclosed invention. Use of the same reference number in multiple figures is intended to designate the same or similar parts. Furthermore, if and when the terms "top," "bottom," "first," "second," "upper," "lower," "height," "width," "length," "end," "side," "horizontal," "vertical," and similar terms are used herein, it should be understood that these terms have reference only to the structure shown in the drawings and are utilized only to facilitate describing the particular embodiment. The extension of the figures with respect to number, position, relationship, and dimensions of the parts to form the preferred embodiment will be explained or will be within the skill of the art after the following teachings of the present invention have been read and understood.

DETAILED DESCRIPTION OF THE INVENTION

Several exemplary embodiments of the graft compression system will now be described with reference to the drawings. Unless otherwise noted, like elements will be identified by identical numbers throughout all figures. The invention (s) illustratively disclosed herein suitably may be practiced in the absence of any element that is not specifically disclosed herein.

Systems and other devices useable for surgical soft tissue graft compression, as well as methods for use of such systems/devices, are disclosed herein. It should be noted that while the exemplary embodiments of the invention described herein are associated with ACL reconstruction surgery, the graft compression systems and methods taught below are not limited to such uses, but could also be equally utilized in connection with other types of surgical procedures involving the use of grafts on other various parts of human and animal bodies.

Figure 1:
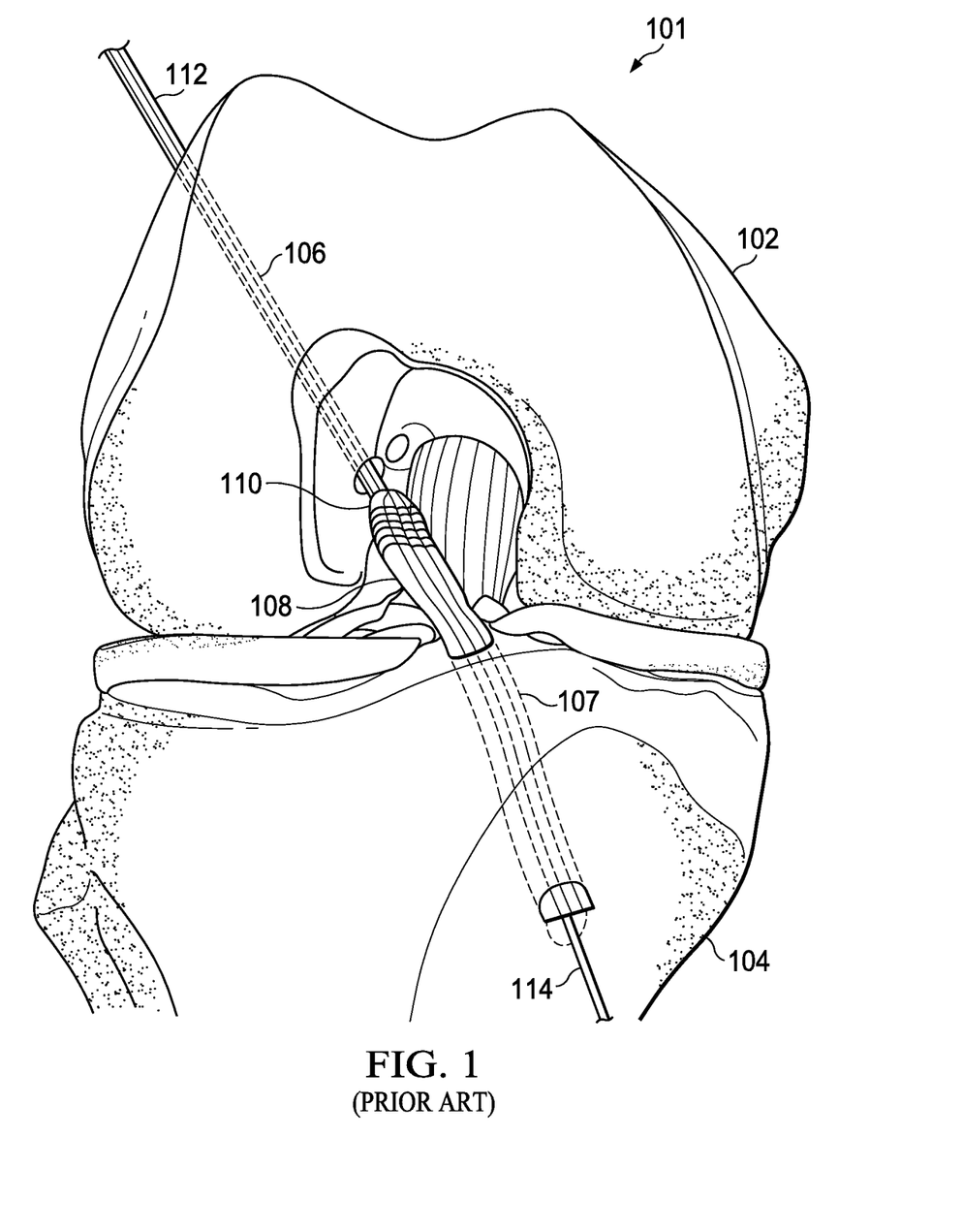
FIG. 1 is a front cut-away view of the surgical placement of a prior art soft tissue graft within a femoral tunnel and tibial tunnel of a patient during ACL reconstruction surgery.

Referring now to FIG. 1, a front cut-away view of the surgical placement of a prior art graft (108) within a femoral tunnel (106) and tibial tunnel (107) of a patient during ACL reconstruction surgery is depicted. As noted above, traditional ACL surgery typically involves the preparation of a soft-tissue tendon graft having a particular diameter, which is positioned within a bone tunnel or tunnels drilled by the surgeon. The bone tunnel(s) are typically sized to have a diameter approximately equal to the diameter of the graft. Accordingly, a reduction of the size of the diameter of the graft will allow tunnels of reduced diameter to be utilized, resulting in less trauma to the patient and quicker recovery times.

The goal of ACL surgery is to restore stability to the injured knee. Grafts used in ACL surgery act as a scaffolding on which new ligament tissue may grow. One example of a type of ACL surgical graft is a patellar tendon autograft that utilizes the patient's own tendon to replace the torn ACL. Other types of ACL surgical grafts include, but are not limited to, hamstring tendons, quadriceps tendons, and cadaver tendons. When preparing an ACL surgical graft prior to surgery, surgical sutures (110) are often tied to the two ends of the graft such that, during positioning of the grant during surgery, a first length of suture line (112) is attached to one end of the graft and extends through the femoral tunnel (106), and a second length of suture line (114) is attached to the other end of the graft and extends through the tibial tunnel (107). Suture lines attached to the ends of the surgical graft allow surgeons to physically manipulate the movement and positioning of the surgical graft via the application of pulling forces on the suture lines.

Figure 2:
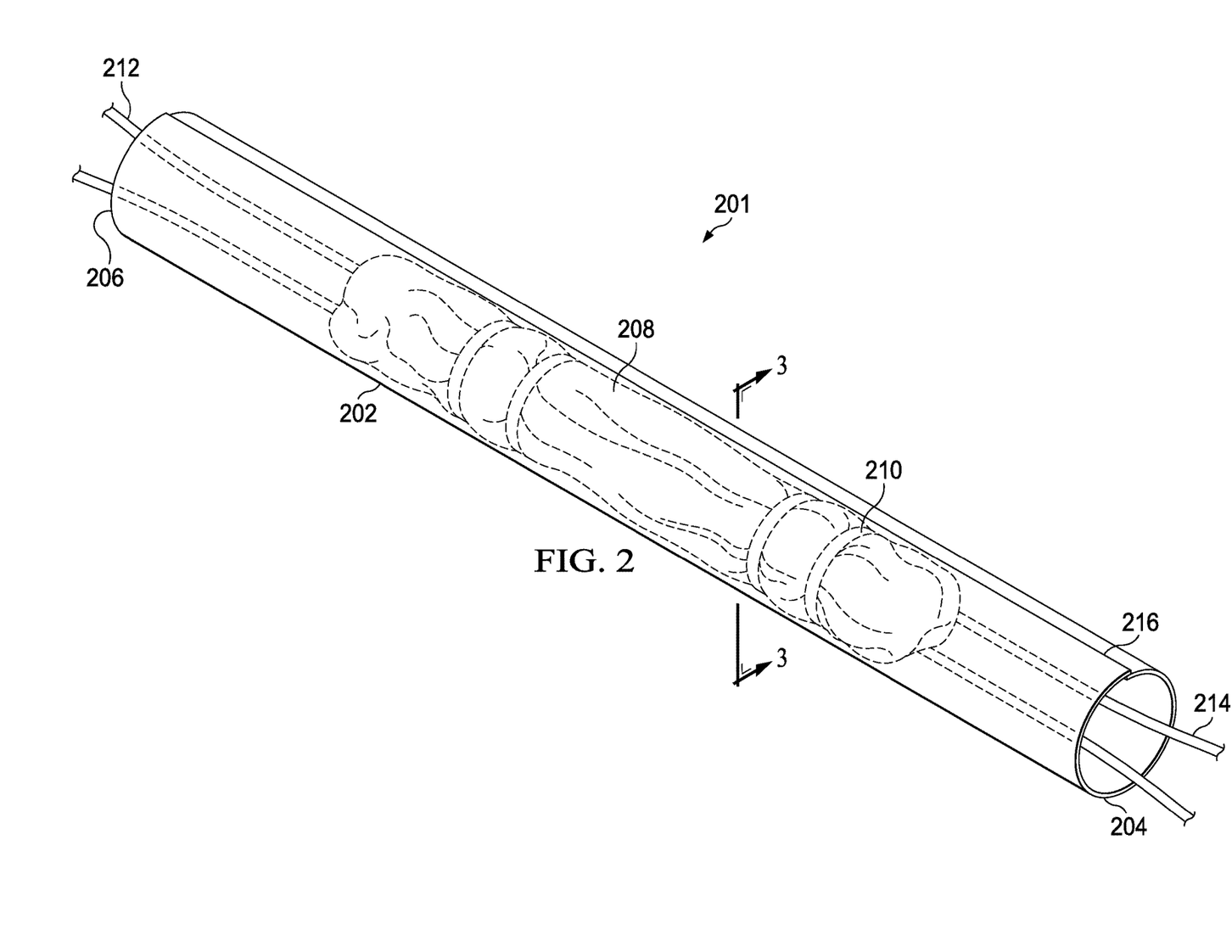
FIG. 2 is a perspective view of one embodiment of an elongate compression tube of the graft compression system, said compression tube having a surgical graft temporarily located within said tube for compression.

Referring now to FIG. 2, depicted is a perspective view of one embodiment of a compression tube (202) of the graft compression system, said compression tube having a surgical graft (208) temporarily located within said tube for compression prior to removal from the tube and placement in a patient during ACL reconstructive surgery or another surgery requiring compression of a graft or other soft tissue element. It is contemplated that surgical grafts commonly used in ACL reconstructive surgery may be used in conjunction with the graft compression system taught herein. In one embodiment, the compression tube (202) is substantially cylindrical in appearance and has substantially cylindrical walls forming a hollow lumen in which a surgical graft may be inserted through openings of the ends of the compression tube. Openings are formed on opposing ends (204, 206) of the compression tube, allowing for the insertion and removal of a surgical graft. Suture lines (212, 214) may be tied or otherwise attached (210) to respective portions of the surgical graft (208). The suture lines (212, 214) aid in maintaining the compactness of the graft, and also provide a means by which the graft may be physically moved and/or otherwise manipulated via pulling forces applied by a surgeon to the suture lines.

In one embodiment, distally oriented suture lines (212) attached to a graft may be "threaded" by a surgeon through the lumen of the compression tube until they emerge through the distal end (206) of said compression tube. The distally oriented suture lines (212) may then be pulled such that the graft is inserted into the compression tube so that the entire graft is enclosed within said compression tube as shown in FIG. 2.

In one embodiment, the elongate compression tube (202) shaft is constructed of a shape memory alloy such as Nitinol that may be "trained" to naturally compress to a predetermined inner diameter. In other embodiments, the compression tube may be constructed of other materials such as stainless steel, aluminum, and other various alloys and polymers that are rigid enough to maintain their overall cylindrical form, yet flexible enough to be compressed with respect to the inside diameter of the lumen of the compression tube and maintain such compression to an acceptable degree. The ability of the compression tube to expand and compress the diameter of the lumen of the tube is provided by the structure of the tube including a discontinuity or gap (216) in the wall of the tube such that when the tube is in an expanded state (not shown), the discontinuity or gap in the tube wall is more readily visible. In other words, while the compression tube appears to be substantially cylindrical in appearance, the tube wall that forms the lumen of the tube is not an uninterrupted wall around the entire circumference of the tube, but rather comprised of a first longitudinal side of a tube wall and a second longitudinal side of a tube wall that are not connected to one another, leaving a gap (216) in the tube wall. When the compression tube is compressed, the first longitudinal side of a tube wall overlaps and can slide over a second longitudinal side of a tube wall as depicted at FIG. 2 at 216, thereby effectively decreasing the inner diameter of the lumen of the compression tube (the outer diameter of the compression tube is also decreased). When a first longitudinal side of a tube wall overlaps a second longitudinal side of a tube wall (or alternatively, can slide underneath the other tube wall), there is the appearance of a line running down the longitudinal length of the compression tube where there is a discontinuity or gap in the tube wall. It is contemplated that water and other substances having lubricating properties can be applied to the outer and/or inner tube walls to aid in the ability of the tube to be compressed.

In one embodiment, a tool (not shown) configured and sized to insert into the gap of the compression tube, may be inserted into such gap. Such tool may be tapered such that as the tool is inserted into the tube gap (216), the diameter of the tube will increase, the tube being constructed of flexible material. By using the tool to increase the diameter of the compression tube, a graft having a diameter larger than the inside diameter of the unaltered compression tube (before insertion of tool into the gap) may be inserted into such compression tube. Once a graft is inserted into the compression tube, the compressive properties of the shape memory alloy (such as Nitinol) or other material used to construct the tube, will act to compress the graft. Thus, the compression tube may act as a first stage of compression of the graft. By inserting the compression tube (and graft enclosed within) into the other components of the graft compression system as discussed below, even further compression of the graft will occur.

Figure 3:
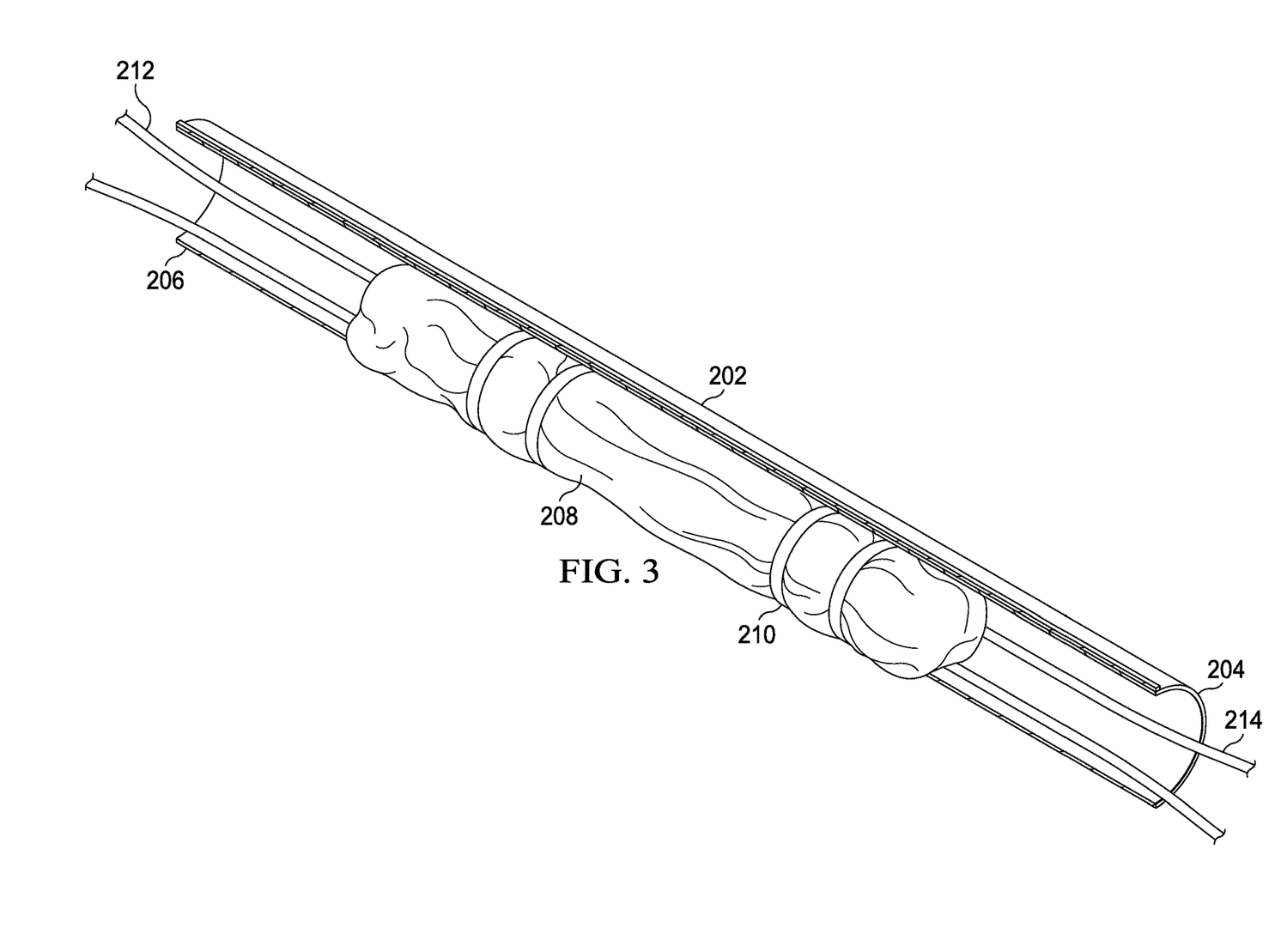
FIG. 3 is a perspective cutaway view of the embodiment of the expandable and compressible elongate compression tube and surgical graft depicted in FIG. 2.

Referring now to FIG. 3, a perspective cutaway view of the embodiment of the compression tube and surgical graft depicted in FIG. 2 is depicted. It should be noted that the length of the graft appearing (208) in FIGS. 2 and 3, as compared to the length of the compression tube (202), is merely intended to illustrate the overall structures of the graft compression system and the relationships between the components thereof. Ideally, a compression tube will have a length selected to be the same length or a larger length as the length of the graft to be compressed within the compression tube. In one embodiment, the length of the compression tube is 120 millimeters. However, in alternate embodiments, the compression tube may have various longer or shorter lengths to accommodate grafts having various lengths used for ACL reconstructive surgery and other types of surgeries. Moreover, the graft compression system taught herein may be utilized regardless of the length differential between the surgical graft to be compressed and the compression tube utilized in compressing such graft. Likewise, the diameter of the compression tube in an uncompressed state will ideally be roughly the same diameter as the diameter of the uncompressed graft to be compressed. Although, as discussed above, it is contemplated that in some embodiments, the compression tube may have a smaller diameter than the uncompressed graft and the compression tube will be at least temporarily expanded to allow the graft to be inserted within. It is also contemplated that in some embodiments of the graft compression system, a funnel type device could be utilized in conjunction with the system to aid in inserting a graft into an end of a compression tube that has a diameter smaller than a surgical graft to be inserted. It is contemplated that water and other substances having lubricating properties can be utilized, in conjunction with suture lines, to assist in the insertion of the graft into the compression tube. In some alternate embodiments of the compression tube, edges of the tube formed on one or both of the ends (204, 206) of the tube may be modified to present a blunter edge or other structure so as to decrease the chance that a graft might be damaged when inserting the graft into the compression tube. Indeed, a protective polymer ring may be inserted over such edge or edges at the ends of the compression tube to protect the graft as it is inserted into the compression tube, the ring(s) being removable prior to insertion of the compression tube into other components of the graft compression system.

Figure 4:
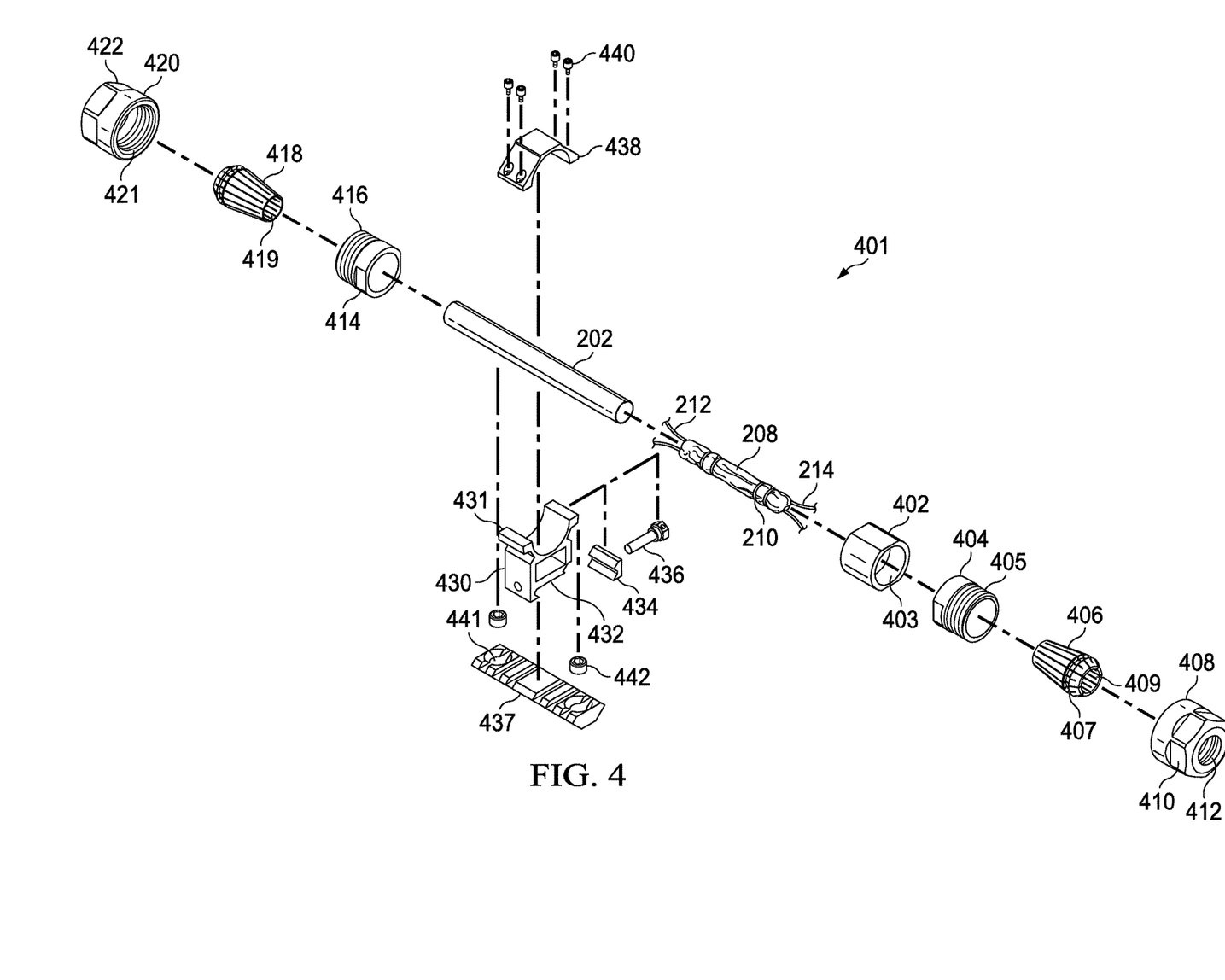
FIG. 4 is an exploded view of one embodiment of the graft compression system.
Figure 6:
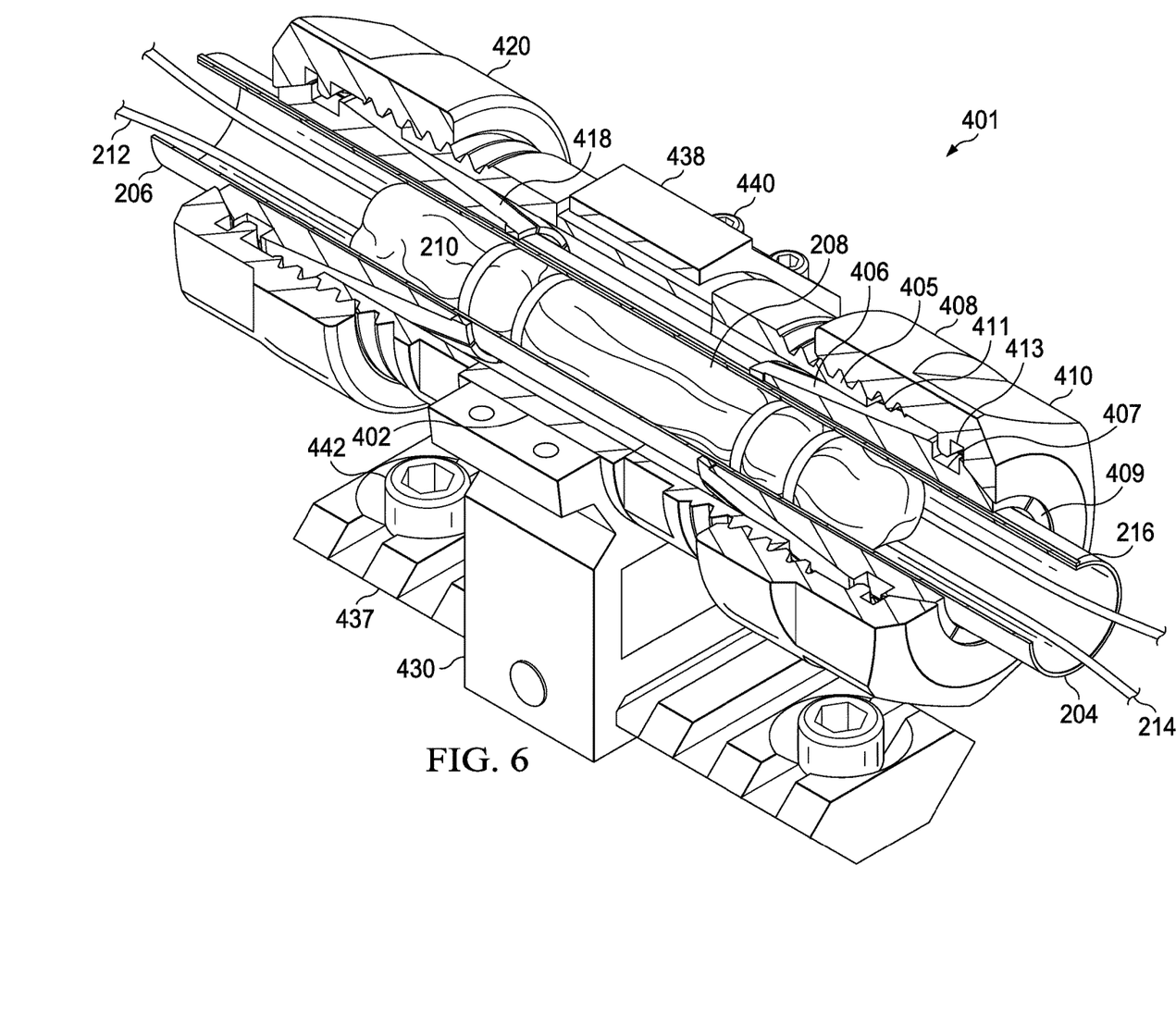
FIG. 6 is a cutaway perspective view of the embodiment of the graft compression system depicted in FIG. 5.

Referring now to FIG. 4, an exploded view of one embodiment of the graft compression system is depicted. In one embodiment, a soft tissue tendon graft (208) may be folded to an appropriate size prior to the initiation of a compression sequence utilizing the graft compression system taught herein. Surgical suture line (212, 214) may be affixed (210) to one or both ends of the graft, and used to insert the graft into the compression tube (202) as described above. In one embodiment of the graft compression system, a compression chamber housing comprising a hollow shaft with an inner diameter greater than an outer diameter of the compression tube, is sized for the insertion of the compression tube within. In one embodiment, the compression chamber housing may be comprised of a first proximal hollow shaft body (404) and a second distal hollow shaft body (414) that are removably fastened or permanently affixed to opposing ends of an intermediary hollow shaft body (402). When attached or affixed to one another, the first proximal hollow shaft body (404), and intermediary hollow shaft body (402) form a continuous lumen into which the compression tube may be inserted as shown in FIG. 6. While the first proximal hollow shaft body (404), second distal hollow shaft body (414), and intermediary hollow shaft body (402) are shown to be three separate bodies in FIG. 4, it is contemplated that a single hollow body may serve the function of a compression chamber sized for the insertion of a compression tube in alternate embodiments of the graft compression system.

In one embodiment, the outer surface of the first proximal hollow shaft body is threaded (405) to mate with correspondingly sized threads (411) formed on the inner wall of the proximal collet nut (408) as depicted in FIG. 6. On the distal side of the graft compression system, the second distal hollow shaft body (414) has threads (416) formed on an outer surface thereof that are configured to mate with correspondingly sized threads formed on the inner wall of the distal collet nut (420) as depicted in FIG. 6. By tightening the proximal collet nut on the first proximal hollow shaft body, an inner collar (413) of the collet nut will engage with a slot (407) formed on the proximal collet (406) to reduce the diameter of the lumen (409) formed within the collet and thereby compress the compression tube (202) and graft positioned (208) within. Similarly, the distal collet nut (420) is likewise configured to threadedly engage the second distal hollow shaft body (414) to compress the inside lumen (419) diameter of the distally positioned collet (418), thereby further compressing the distal end of the compression tube and surgical graft within.

Still referring to FIG. 4, in one embodiment of the graft compression system, the proximal (405), intermediary (402), and distal (414) hollow shaft bodies which together form the compression chamber housing are constructed of metal such as, for example, stainless steel, but may in alternate embodiments may be constructed of other types of metals, alloys, or polymers that are capable of easy sterilization utilizing common sterilization systems employed by hospitals and other surgical centers. Off-the-shelf ER type collets as depicted in FIG. 4 have a tapered outer surface and a substantially cylindrical inside diameter. In the embodiment of the graft compression system depicted in FIG. 4, the collets (406, 418) are configured to be positioned inside the respective ends of the distal and proximal hollow shaft bodies of the compression chamber. The larger diameter ends of said collets are, in the embodiment of the graft compression system shown in FIG. 4, oriented towards the respective ends of graft compression system.

In one embodiment of the graft compression system, a bracket similar to riflescope rings may be used to secure and stabilize the proximal, distal, and intermediary hollow shaft bodies to a rail (437) that may in turn be secured to a working board or other structure located in an operating room or other space designed for preparation of the surgical graft prior to surgery. The stabilizing bracket may in one embodiment comprise an upper semi-circular ring (438)

configured to wrap around the top of the intermediary hollow shaft body (402) and be fastened to a lower semi-circular ring (431) configured to cradle the bottom of the said intermediary hollow shaft body. A plurality of screws may be utilized to fasten the upper semi-circular ring (438) to the lower semi-circular ring (431). The lower semi-circular ring (431) may further include lower structures similar to those of riflescope rings, including a slot (432) configured to mate with a rail body (437). An adjustable slot wall (434) configured to abut the slot structure (432) of the lower semi-circular ring (431) may be tightened and loosened using a screw (436), thereby securing the lower semi-circular ring (431) structure to a rail (437), which in turn may be secured to a working board (504) using screws (not shown) and nuts (442) as depicted in FIG. 5.

Figure 5:
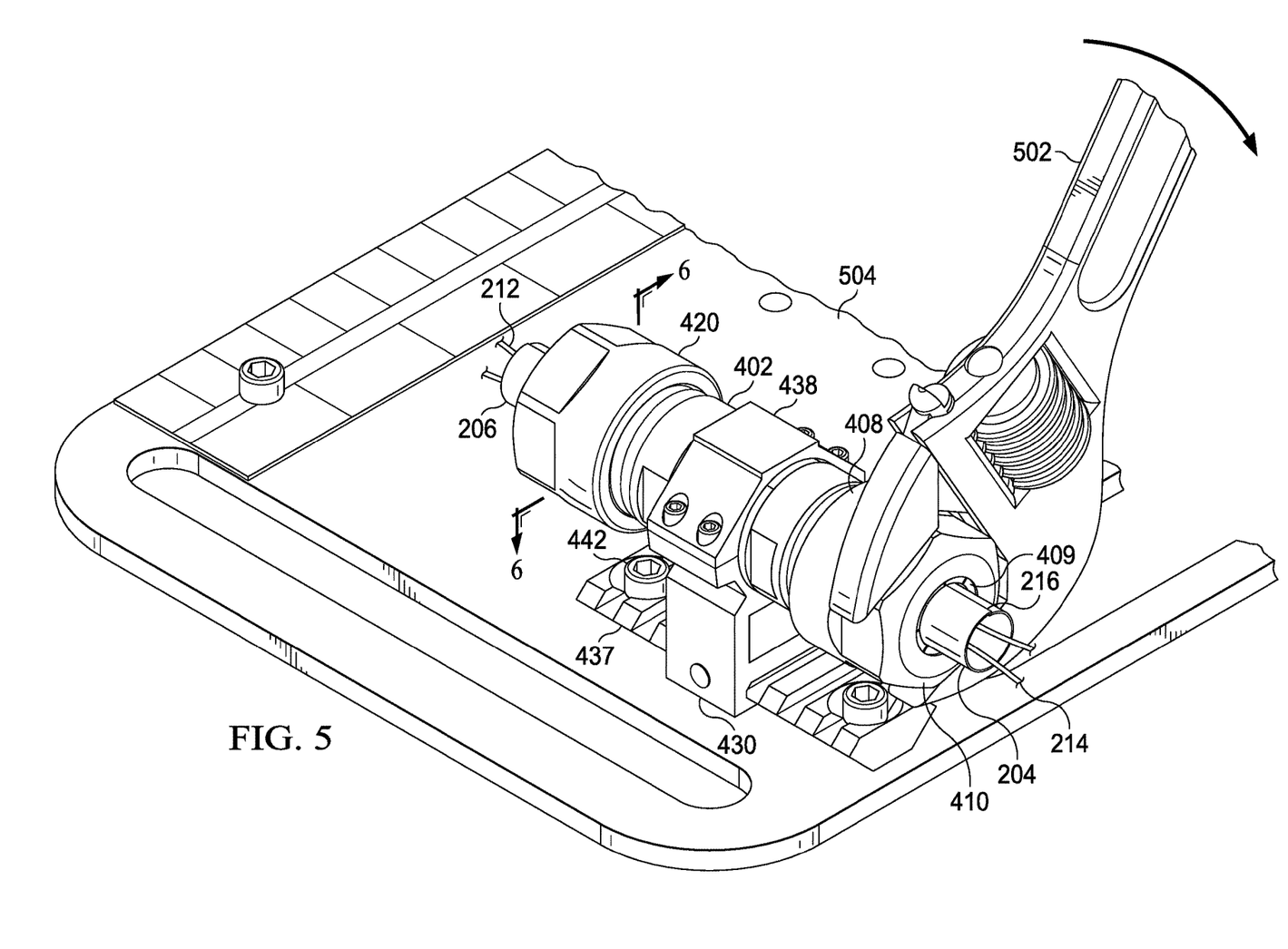
FIG. 5 is a perspective view of the embodiment of the graft compression system depicted in FIG. 4, said system having been mounted on a working board, and further depicting a wrench attached to an outer surface of a first proximal collet nut.

Referring now to FIG. 5, depicting a perspective view of the embodiment of the graft compression system depicted in FIG. 4, said system having been mounted on a working board (504), and further depicting a wrench (502) attached to an outer surface of a first distal collet nut. The wrench is configured to grasp the hexagonal surfaces (410, 422) of the respective collet nuts such that wrench might turn said collet nuts to tighten or loosen the collets. In one embodiment of the graft compression system, the collet nuts (408, 420) are sized and structurally configured to mate with a respective distal or proximal hollow shaft body to which it is attached. Each of the proximal and distal collets is nested within a respective proximal and distal hollow shaft body. An internal collar protrusion (FIG. 6 at 413 showing internal collar protrusion on proximal collet nut) formed on each collar nut is configured to engage a respective adjacent collet slot (FIG. 6. at 407 showing collar slot on proximal collet). When rotated by a user using a wrench or other tool, the collet nut works to selectively adjust the working inside diameter of the collet. Each collet has an opening on each end of the collet such that, when two or more collets are aligned within the hollow shaft bodies of the graft compression system as described herein, a passageway is formed through the system, allowing for the insertion and removal of a compression tube configured to hold soft tissue grafts. In one embodiment, an ER type collet having a particularly sized inner diameter (for example, a 10 millimeter inside diameter) that is optimized for a graft of a particular size, or selected for a particular type of surgery or particularly sized bone tunnel or socket. Typical collets are capable of inside diameter compression of 1-2 millimeters.

Still referring to FIG. 5, a wrench (502) or similar instrument may be utilized to rotate each collet nut (408, 420) in a counterclockwise direction providing for the closing or tightening of the respective collet to which it is mated. As the collet nut is rotated, the collet's inside diameter will decrease, resulting in the compression of the graft. A collet nut may be rotated in a counterclockwise direction if it is desired to expand the inside diameter of the lumen of the respective collet. Users of the graft compression system will ideally wait for a predetermined period of time (for example, five minutes) prior to removal of the compression tube from the graft compression system. Such a waiting period will aid in preventing the graft from experiencing premature expansion. While ER type collets have been described herein as one type of compressive device that may be utilized to provide compressive force along a lumen of the graft compression system, other types of collets and compressive devices may also be utilized to the extent that such compressive devices are capable of providing compressive forces along all or a portion of the length of a compression tube.

While the preferred embodiment of the graft compression system described herein is configured for manual operation, allowing a surgeon to utilize simple, easily sterilized tools (such as a wrench) to operate the system, it is contemplated that alternate embodiments of the graft compression system may allow for the use of power tools having rotary motors to engage the collet nuts or to otherwise actuate other types of compression devices that may be utilized as substitutes for collets.

The graft compression system described and depicted herein provides many advantages in the field of ACL reconstruction surgery and other types of surgeries involving the use of grafts. One advantage realized is that the graft compression system is capable of being easily sterilized as it is composed of relatively simple and easily assembled/disassembled components. Another advantage of the graft compression system is that it is capable of being manually operated by surgeons and other operating room personnel, requiring only the use of simply hand tools to actuate the compression system. Another advantage of the graft compression system is that it is capable of effectively reducing the overall volume of a graft by 50% or more, meaning that surgeons will be able to significantly reduce the size/volume of bone tunnels and sockets. Thus, as a result, patients will experience less tissue trauma, swelling, and pain.

Other advantages of the graft compression system and its ability to effectively reduce the diameter of a graft, arise from the relatively "tight" fit of the graft within the bone tunnel or socket into which it may be inserted. Once inserted, the graft will rehydrate and expand, creating a biologic compressive fit within such bone tunnel or socket. Such a compressive fit will result in a well-fixed graft, making it unnecessary to utilize interference screws and buttons to affix the graft. The nature of the well-fixed graft arising from the use of compressed grafts will also act to minimize micro-motion, thus reducing scarring. Other benefits arising from use of the graft compression device include faster tissue recovery, improved healing environment, and overall improved outcomes.

Referring now to FIG. 6, depicted is a cutaway perspective view of the embodiment of the graft compression system depicted in FIG. 5. As noted above, an internal collar protrusion (413) formed on each collar nut is configured to engage a respective adjacent collet slot (407). As those of ordinary skill in the art will appreciate, a collet nut, when rotated by a user, works to selectively adjust the working inside diameter of the collet (increasing or decreasing the inside diameter of the collet, depending on the direction the collet nut is rotated). The compression tube (202) may be inserted into an opening (409) in the proximal collet (406) or distal collet (418), which leads to a lumen within the hollow shaft bodies (404, 402, 414). It is contemplated that both collet nuts (408, 420) may be tightened such that the respective collets to which they are engaged will compress the compression tube and in turn the surgical graft within such tube. It is also contemplated that one portion of the compression tube may be compressed, and the compression tube incrementally moved down the lumen of the hollow shaft bodies, and compressed at each incremental step such that the entire length of the compression tube (and graft within) may be subjected to more direct compressive forces of the collet(s). By this method of compression, it would be possible to configure an alternate embodiment of the graft compression system to utilize only a single side of the system depicted in FIG. 6—in other words, it would be possible in alternate embodiments to utilize only a single collet nut and collet to incrementally compress a length of a compression tube.

It is further contemplated that the graft compression system taught herein may be used to compress a graft in a single stage of compression, or in multiple stages of compression by using removable collets having progressively smaller inside diameters. For example, in a first stage of compression, collets having inside diameters compressible from a 10-millimeter diameter to a 9-millimeter diameter may be initially inserted into the respective ends of the hollow shaft bodies. A compression tube containing a surgical graft may be inserted and compressed in the manner described above. Using a tool such as the T-handle collet check (701) described in connection with FIG. 7 below, the compression tube may be removed and the compression better maintained. The first set of collets may then be removed and a second set of collets compressible from a 9-millimeter inside diameter to an 8-millimeter diameter may be inserted into the graft compression system and the compression tube reinserted into the graft compression tube for a second stage of compression. In this manner, the graft compression system may be used to progressively compress a surgical graft in multiple stages prior to use in surgery.

Figure 7:
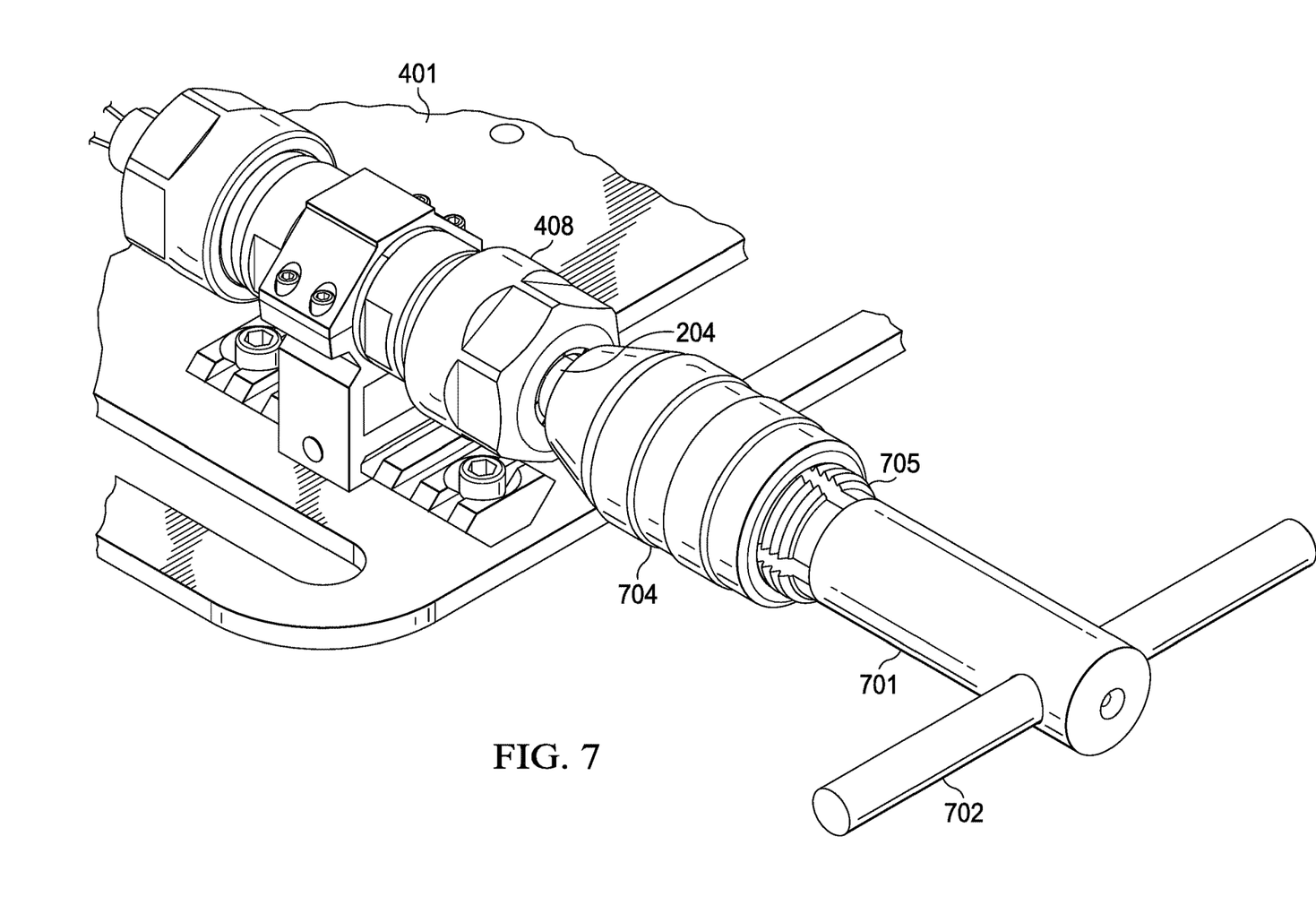
FIG. 7 is a perspective view of the embodiment of the graft compression system depicted in FIG. 5, adjacent to an embodiment of a T-handle collet chuck attached to and maintaining the compression of a proximal end of the expandable and compressible elongate compression tube.

Referring now to FIG. 7, depicted is a perspective view of the embodiment of the graft compression system depicted in FIG. 5, adjacent to an embodiment of a T-handle collet chuck (701) attached to and maintaining the compression of a distal end of the expandable and compressible elongate compression tube. Depending on the materials used to construct the compression tube, it may be necessary to take steps to maintain the compressed diameter of a compression tube after the graft compression system has been used to compress the compression tube and surgical graft within. A T-handle collet chuck having a handle (702) on one end and a threaded chuck (704) for compressing an internal collet (not shown), may be tightly attached around a proximal end (204) of the compression tube such that the diameter of the compression tube does not increase. The collet chuck may then be used to remove the compression tube from the hollow shaft bodies and collets to deliver and insert such compression tube into a surgical cannula or portal holder device, or other type of surgical device being used to place the graft into the surgical site on the patient. Alternatively, such a collet chuck may be used to maintain the compressed diameter of the compression tube, and to remove such compression tube from the graft compression system while a first set of collet devices are removed and a new set of collet devices are inserted in conjunction with a multi-stage compression sequence as described above.

Figure 8:
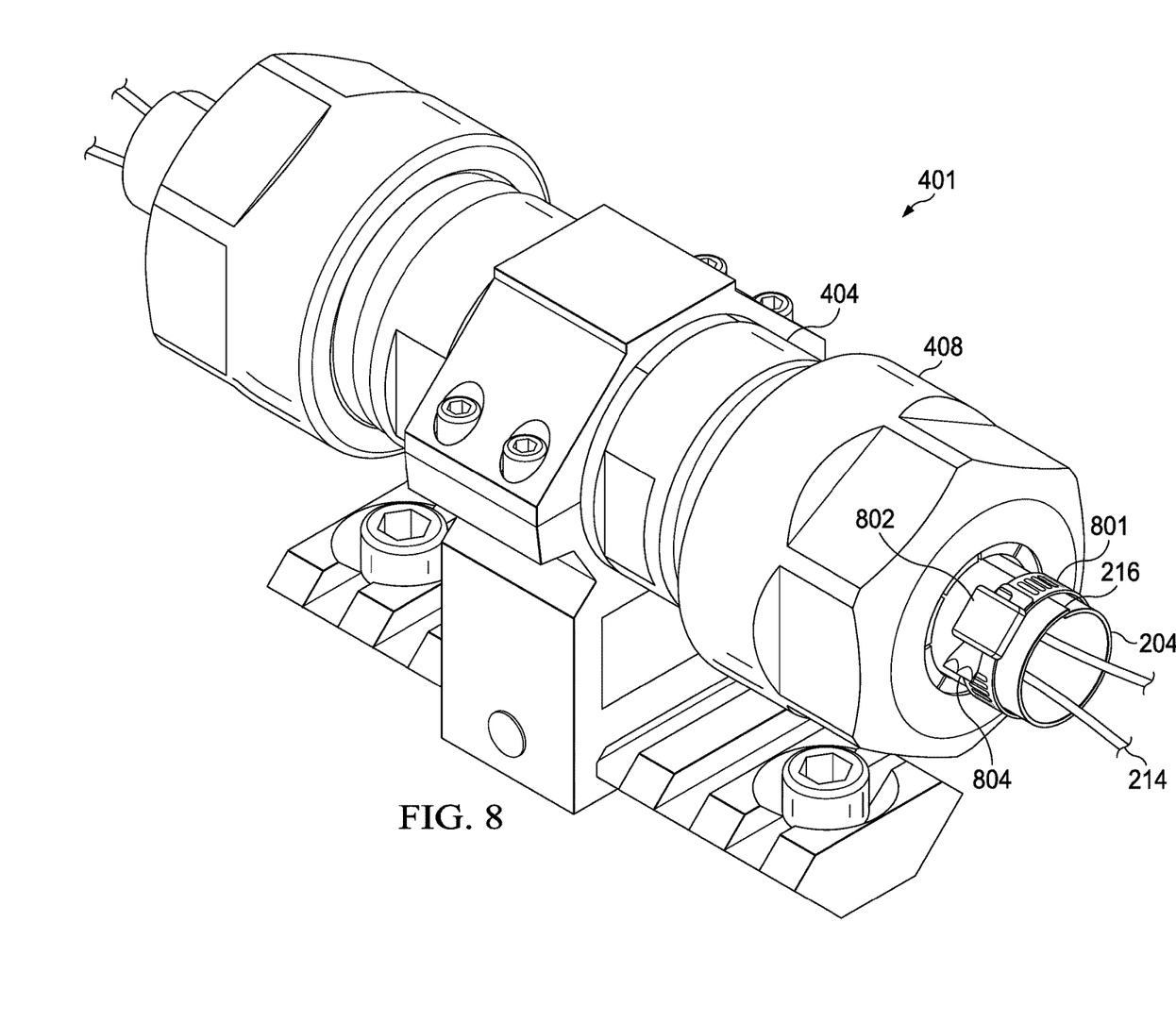
FIG. 8 is a perspective view of the embodiment of the graft compression system depicted in FIG. 5, having an adjustable hose clamp attached to and maintaining the compression of a proximal end of the expandable and compressible elongate compression tube.

Referring now to FIG. 8, depicted is a perspective view of the embodiment of the graft compression system depicted in FIG. 5, having an adjustable hose clamp (801) attached to and maintaining the compression of a proximal end (204) of the expandable and compressible elongate compression tube (202). Once at least a first stage of compression of the compression tube and surgical graft has been completed, an adjustable hose clamp (801) may be tightly fastened to an end of the compression tube using a screw (804) and nut (802) of the clamp such that the diameter of the compression tube does not increase when the tube is removed from the graft compression system. The compression tube may then be removed from the graft compression system, with additional hose clamps fastened along the length of the compression tube. The hose clamp(s) may be used to maintain the compressed diameter of the compression tube until such time as the compression tube may be inserted into a surgical cannula or portal holder device, or other type of surgical device being used to place the graft into the surgical site on the patient. Alternatively, such hose clamp(s) may be used to maintain the compressed diameter of the compression tube while a first set of collet devices are removed and a new set of collet devices are inserted in conjunction with a multi-stage compression sequence as described above. For such a purpose, the hose clamps may be sequentially removed as the compression tube is reinserted into the hollow shaft bodies and collets for the next stage of compression.

Figure 9:
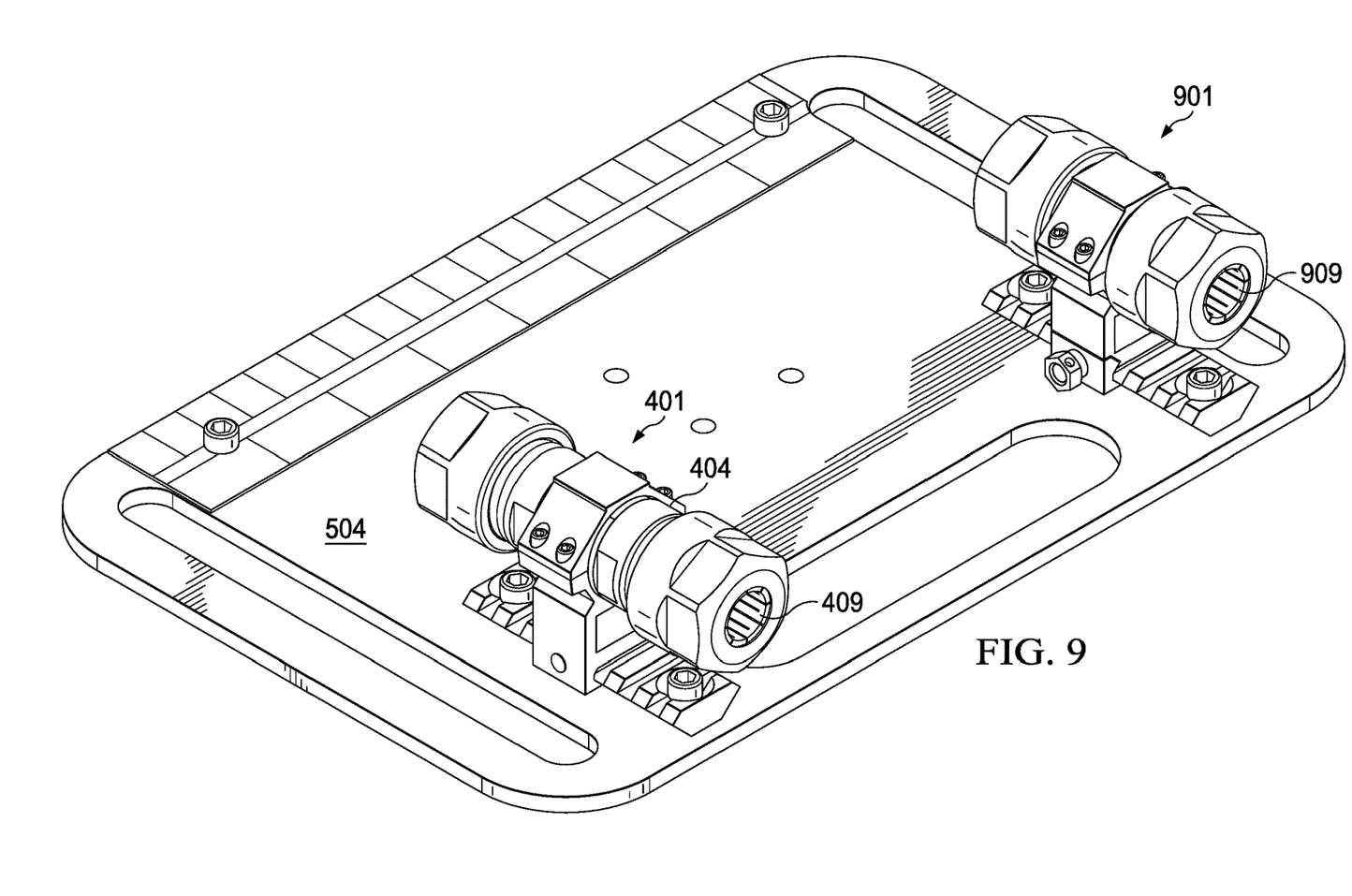
FIG. 9 is a perspective view of the embodiment of the graft compression system depicted in FIG. 5 mounted on a working board adjacent to an alternate embodiment of the graft compression system having a compression shaft with a decreased length.

Referring now to FIG. 9, depicted is a perspective view of the embodiment of the graft compression system that is depicted in FIG. 5, said system being mounted on a working board adjacent to an alternate embodiment of the graft compression system having a compression chamber shaft with a decreased length. By utilizing two or more graft compression devices in close proximity to one another, advantages may be realized in that surgical grafts of various lengths may be compressed without having to make adjustments to the lengths of the hollow shaft bodies. It is contemplated that intermediary hollow shaft bodies having various lengths may be removably fastened to distal and proximal hollow shaft bodies to provide the surgeon with the ability to select an optimal length of a compression chamber. However, in some circumstances, it may be preferable to have ready access to one or more graft compression systems having compression chambers of different lengths immediately available for use without it being necessary to disassemble and reassemble the graft compression system. Another advantage of utilizing multiple graft compression systems in close proximity to one another is that such a configuration gives the surgeon the ability to utilize different sized collets in each graft compression system. In this manner, a surgeon could perform multiple stages of compression without having to disassemble and reassemble graft compression systems to remove and insert progressively smaller collet sets.

In one embodiment, a surgical graft compression system may comprise a compression chamber having an elongate hollow shaft body, said hollow shaft body having a first proximal end and a second distal end, each of said first proximal end and said second distal end having outer surfaces on which threaded surfaces are formed; a proximal first collet nut configured to threadedly fasten to said first proximal end of said elongate hollow shaft body; a distal second collet nut configured to threadedly fasten to said first end of said elongate hollow shaft body; a proximal first collet configured for insertion into said proximal first collet nut; a distal second collet configured for insertion into said distal second collet nut; and a hollow tube having a lumen with a compressible diameter, said hollow tube being configured for removable insertion into said proximal first collet, said compression chamber, and said distal second collet. In another embodiment, said proximal first collet nut includes an internal collar protrusion that is configured to engage a collar slot formed on an outer surface of said proximal first collet. In one embodiment, the counterclockwise rotation of said proximal first collet nut causes an inner collet lumen of said proximal first collet to have decreased diameter. In one embodiment, a first semi-circular upper bracket is fastened to a second semi-circular lower bracket, wherein at least a portion of said compression chamber is secured within said first semi-circular upper bracket and said second semi-circular lower bracket. In one embodiment, said second semi-circular lower bracket is mounted to a board. In another embodiment, a surgical graft compression system may comprise a compression chamber having an elongate hollow shaft body, said hollow shaft body having a first proximal end and a second distal end, said first proximal end having outer surfaces on which threaded surfaces are formed; a collet nut configured to threadedly fasten to said first proximal end of said elongate hollow shaft body; a collet configured for insertion into said collet nut; and a hollow tube having a lumen with a compressible diameter, said hollow tube being configured for removable insertion into said collet and said compression chamber.

The inventions described herein may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes that come within the meaning and range of equivalency of the claims are embraced therein.

I claim:

1. A surgical graft compression system comprising:
   a compression chamber having an elongate hollow shaft body, said hollow shaft body having a first proximal end and a second distal end, each of said first proximal end and said second distal end having outer surfaces on which threaded surfaces are formed;
   a proximal first collet nut configured to threadedly fasten to said first proximal end of said elongate hollow shaft body;
   a distal second collet nut configured to threadedly fasten to said first end of said elongate hollow shaft body;
   a proximal first collet configured for insertion into said proximal first collet nut;
   a distal second collet configured for insertion into said distal second collet nut; and
   a hollow tube having a lumen with a compressible diameter, said hollow tube being configured for removable insertion into said proximal first collet, said compression chamber, and said distal second collet.

2. The surgical graft compression system of claim 1, wherein said proximal first collet nut includes an internal collar protrusion that is configured to engage a collar slot formed on an outer surface of said proximal first collet.

3. The surgical graft compression system of claim 2, wherein the counterclockwise rotation of said proximal first collet nut causes an inner collet lumen of said proximal first collet to have decreased diameter.

4. The surgical graft compression system of claim 1, further comprising a first semi-circular upper bracket fastened to a second semi-circular lower bracket, wherein at least a portion of said compression chamber is secured within said first semi-circular upper bracket and said second semi-circular lower bracket.

5. The surgical graft compression system of claim 4, wherein said second semi-circular lower bracket is mounted to a board.

* * * * *